United States Patent [19]

Roeher et al.

[11] Patent Number: 5,503,624
[45] Date of Patent: Apr. 2, 1996

[54] INFUSION SYSTEM WITH CONTROL DEVICE

[75] Inventors: Otfried Roeher, Dresden; Roberto Belke, Hamburg; Steffen Korth, Erfurt, all of Germany

[73] Assignee: B. Braun Melsungen AG, Melsungen, Germany

[21] Appl. No.: 372,811

[22] Filed: Dec. 23, 1994

[30] Foreign Application Priority Data

Dec. 29, 1993 [DE] Germany .......................... 43 44 872.0

[51] Int. Cl.$^6$ .................................................. A61M 31/00
[52] U.S. Cl. .................................................. 604/65
[58] Field of Search .......................... 604/65–67, 30–34, 604/48–53, 65–67, 207, 246–249; 128/DIG. 12, DIG. 13

[56] References Cited

PUBLICATIONS

Hao Ying, et al., "Expert–system–based fuzzy control of arterial pressure by a drug infusion", Medical Progress through Technology 13, 203–215 (1988).

*Primary Examiner*—C. Fred Rosenbaum
*Assistant Examiner*—Manuel Mendez
*Attorney, Agent, or Firm*—Loeb and Loeb

[57] ABSTRACT

The infusion system is provided with a control device (10) wherein a plurality of influence factors with different physiological action mechanisms, i.e. a plurality of semantic domains, is considered as fuzzy information in the automatic dosing of drugs and the semantic significance of the individual domains is taken into account. The control device (10) for controlling at least one infusion apparatus (21) comprises a plurality of fuzzy control units (17,19) structured in a hierarchical system. On a first hierarchical levels, all linguistic variables, measurement values and derived values are examined by a semantic analyzer (16) with regard to the significance of their contents for the various semantic domains. In a unit (18) for evaluation of semantic domains, the results of the above examination are passed through a plurality of evaluation stages to draw conclusions on the operation on a second hierarchical level on which each semantic domain is represented by a fuzzy control unit (19) of its own. By the continuous semantic analysis on the first hierarchical level and the selective controlling of the fuzzy control units (19) on the second hierarchical level, the qualitatively different components of influence as well as the changes in the patient's condition occurring during the treatment, are reliably interpreted in their complex interaction and corresponding to their semantic significance and are included in the automatic dosing of drugs.

5 Claims, 7 Drawing Sheets

Semantic domain "hypotension"
Subdomain "blood pressure decrease"
Subdomain "trend of hypotension"
Subdomain "subjective complaints"
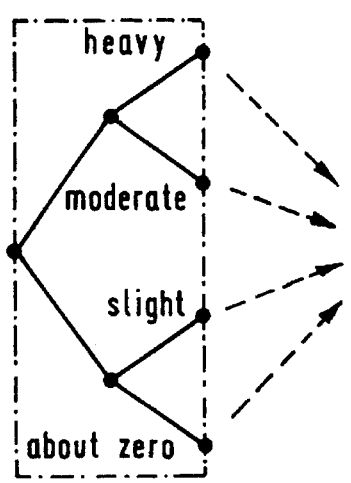
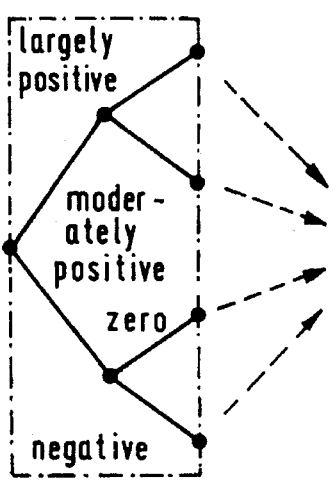
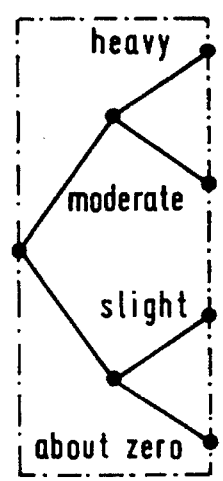
FIG.2a

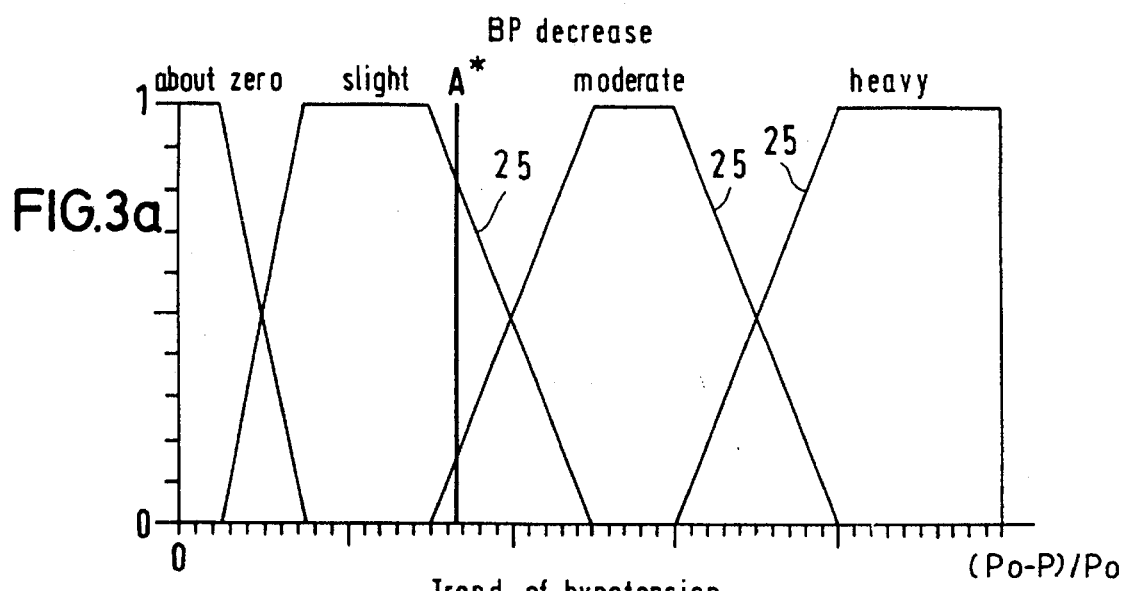
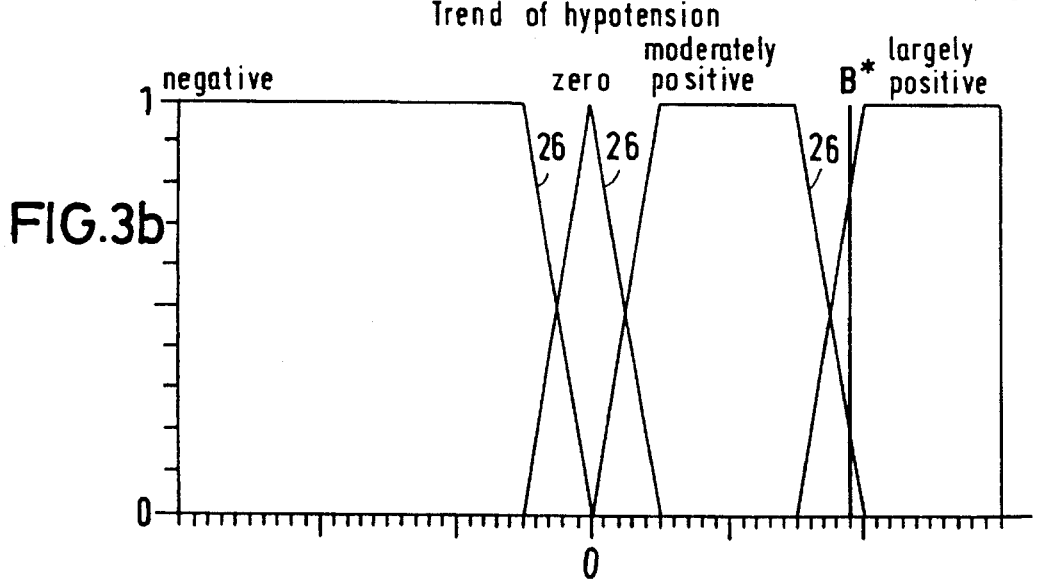
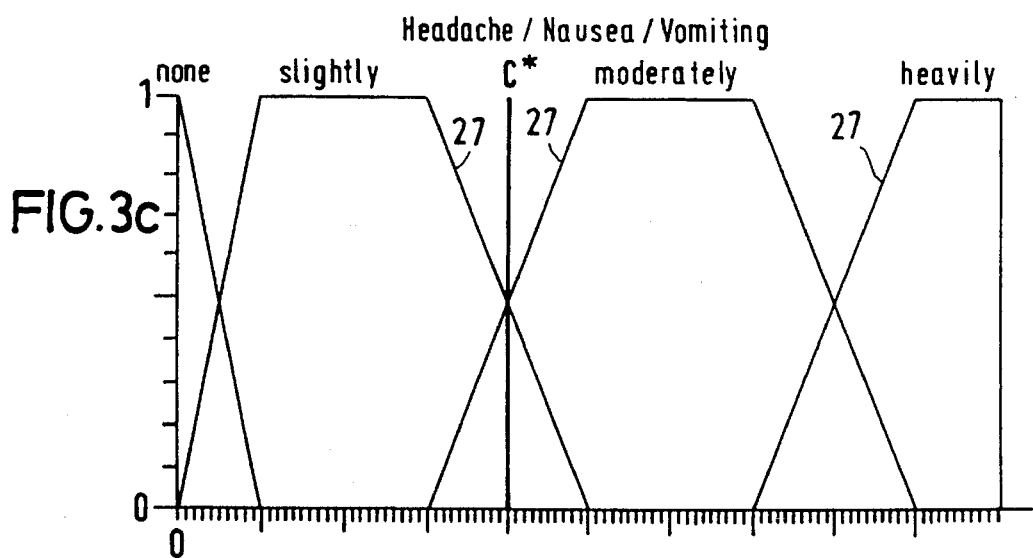

calculation of the center of gravity (d*: abscissa value of the center of gravity)

INFUSION SYSTEM WITH CONTROL DEVICE

BACKGROUND OF THE INVENTION

The invention is directed to an infusion system having a control device for automatically adapting the dosage of drugs to the multi-factorial influences of the patient's condition which can change over time.

In many cases, infusion of drugs is an indispensable therapeutical measure for maintaining the vital functions of the human organism. Particularly during extracorporeal purification of the blood in patients suffering from; chronic kidney diseases, or after extensive surgical interventions or in case of large blood loss due to injuries, the frequent complications are characterized by multi-factorial influences with high non-linearities. Although the mechanisms of the effects of the individual factors are known in qualitative terms, hardly any clearance has been achieved concerning their complex interaction. Thus, typically, knowledge on the causal interdependencies underlying the complications is largely fuzzy.

Due to their deterministic control characteristics and the associated algorithms, numerous infusion systems are restricted to the crisp (deterministic) knowledge on the control mechanisms of the human organism.

In many known cases, the control devices are used on the basis of a black-box model which is valid under stationary conditions or quasi-stationary conditions. Therefore, such control devices react insufficiently or not at all on the spontaneous sensitivity changes of the endogenous regulatory system. Further disadvantages arise in processes involving long idle times, as normally occurring in the human organism during infusion of drugs.

In other known infusion systems, use is made of control structures having adaptive properties. In these systems, the adapting of the infusion rate to the varying condition of the patient is performed through fixedly predetermined algorithms, which partially even allow predictions on the period up to the onset of the drug's effect. The algorithms have been obtained on the basis of individual components of influence of the multi-factorial control mechanisms. Therefore, control devices of the above type provide useful results only as long as the underlying causal connections are really decisive for the current effect of the drug infusion.

However, as apparent from medical practice, complications occurring in the human organism often have their origin in qualitative changes occurring in the complex interaction of multi-factorial components. These phenomena can be represented only as fuzzy (probabilistic) information in the form of probabilistic relations and linguistic variables.

Thus, applications of the above kind require infusion systems adapted to detect and evaluate a plurality of different components of influence in the form of fuzzy information and to involve these components in the automatic controlling of the dosage of drugs corresponding to their semantic significance. This applies particularly to medical applications such as extracorporeal blood purification wherein additional components of influence will result directly from the intended therapeutical purposes of the treatment. In such applications, the interaction between the dosage of the drug and the target parameters of the treatment, such as ultrafiltration rate, overall dehydration, sodium balance and other important control parameters, must be continuously observed.

Due to their deterministic structure, the above outlined known control devices are not suited to fulfill these demands.

Some known blood pressure control devices, used in surgery for monitoring purposes during and after a surgical intervention, are designed for processing fuzzy knowledge on the basis of fuzzy logic (H. Ying et al, "Expert-system-based fuzzy control of arterial pressure by drug infusion", in: Medical Progress through Technology, Kluner Academic Publishers, Dordrecht, Netherlands, 198, pp. 203 thru 215).

Also fuzzy control devices of this type do not meet the above demands for the following reasons: The medical purpose of blood pressure control consists exclusively in keeping the blood pressure constant during and after a surgical intervention. The blood pressure and values derived therefrom, such as a deviation from the desired value of the blood pressure (error) and the change over time of these deviations (rates), are the only criteria used for the operation of the fuzzy control device. Thus, control is restricted to a sole semantic domain. Additional influence factors caused by a simultaneously performed therapeutical measure are left unconsidered.

Therefore, it is an object of the invention to provide an infusion system comprising a control device which actively includes a plurality of influence values having different physiological action mechanisms, i.e. a plurality of semantic domains, into the automatic dosing of drugs as fuzzy information and which, in doing so, takes into account the different semantic significances of the different domains.

SUMMARY OF THE INVENTION

The infusion system according to the invention comprises a control device provided for controlling at least one infusion apparatus and including a plurality of fuzzy control devices arranged in the structure of a hierarchical system.

The detected measurement values and/or linguistic variables are received by a measurement value central processing unit, and this unit computes further values which are essential for evaluation.

On a first hierarchical level, all linguistic variables, measurement values and derived values are examined by a semantic analyzer with regard to the significance of their contents for the various semantic domains. The semantic analyzer comprises a first fuzzy control unit which links all input values to their appertaining fuzzy sets (fuzzification), and, through integrated fuzzy logic, in each semantic domain detects the overriding membership for all conditions defined within the associated control base.

By a likewise integrated unit for semantically evaluating the domains, the results of the above detection are passed through a plurality of evaluation stages to draw conclusions on the operation of a second hierarchical level on which each semantic domain is represented by a further fuzzy control unit of its own.

The total semantic evaluation result of each individual domain is transmitted by the semantic analyzer of the first hierarchical level in the form of a crisp control value (defuzzification) to the associated further fuzzy control unit of the second hierarchical level. Each further fuzzy control unit selectively receives all of the input values which have been detected for its domain by the measurement value processing unit.

Further, each fuzzy control unit is provided with a domain-specific control base and with modules for fuzzification, logical linking, fuzzy inference and defuzzification.

During the automatic dosing of drugs, the hierarchical structure and operation of the infusion system provide for an approximate reflection of the medical decision processes. Particularly, due to the continuous semantic analysis on the first hierarchical level and the selective controlling of the fuzzy control units on the second hierarchical level, it is safeguarded that the qualitatively different components of influence as well as the changes occurring in the course of the treatment are detected in their complex interaction and corresponding to their semantic significance and are considered during the automatic dosing of drugs.

BRIEF DESCRIPTION OF THE DRAWINGS

An embodiment of the invention will be explained in greater detail hereunder with reference to the drawings.

FIGS. 2a to 2c show diagrams of the three semantic domains, "hypotension", "plasma volume" and "ultrafiltration" along with their subdomains, FIG. 3 illustrates the membership functions (fuzzy sets) of three variables used as decision criteria in the first fuzzy control unit.

DESCRIPTION OF A PREFERRED EMBODIMENT

Figure 1:
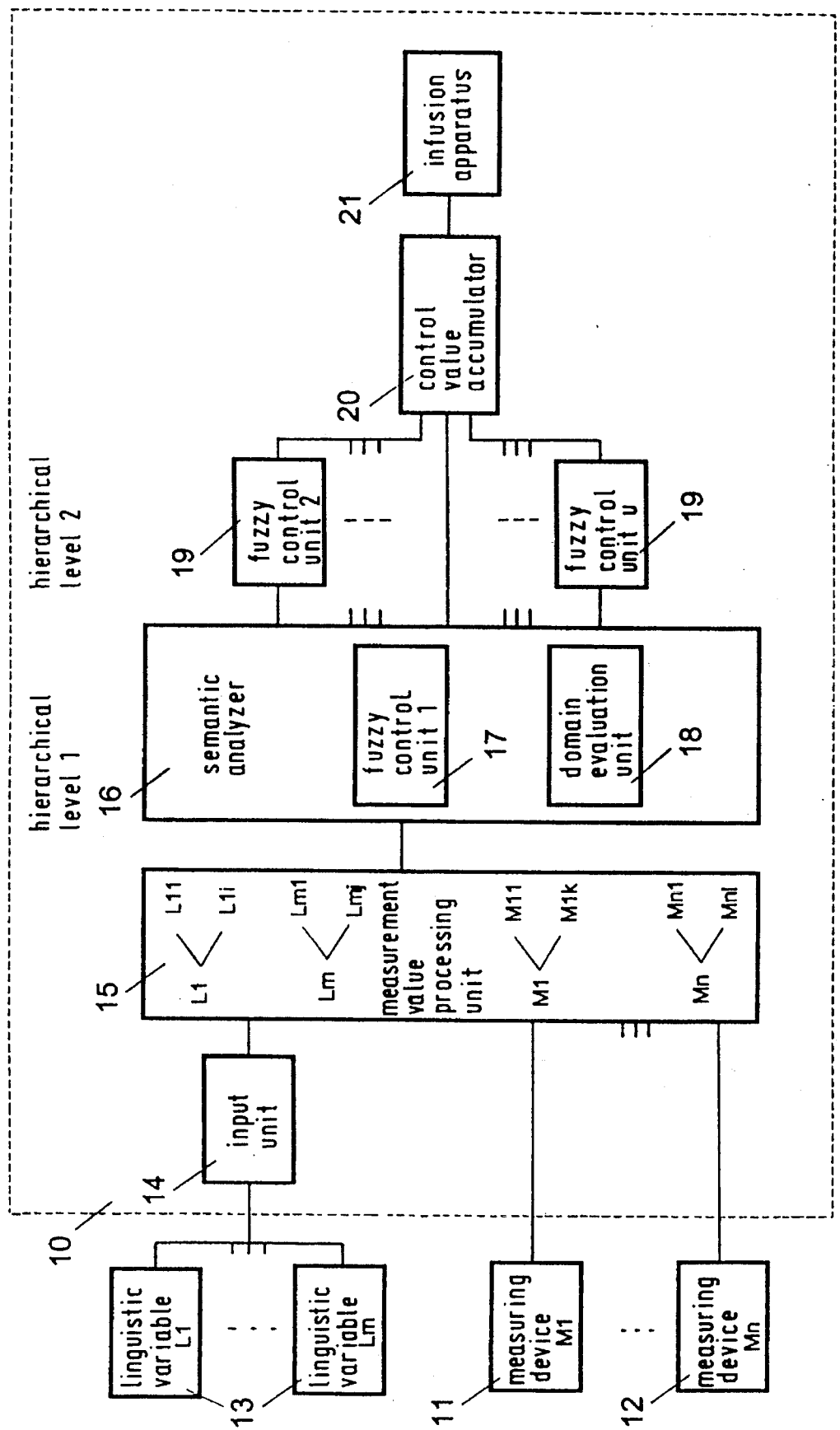
FIG. 1 shows a systematic representation of an infusion system for extracorporeal blood purification in patients having chronic kidney diseases.

The infusion system according to FIG. 1 comprises a hierarchically structured control device 10 having n different measuring devices 11,12 connected thereto. Since the infusion system is to be used for stabilizing the blood pressure during extracorporeal blood purification, the measuring device 11 is designed as a blood pressure measuring device for measuring the systolic and/or mean arterial blood pressure of the patient as a measurement value $M_1$.

The further measuring devices 12 are used for measuring other measurement values $M_2 \ldots, M_n$ which are relevant for blood pressure stabilization during extracorporeal blood purification. Normally, the first values to be considered in this regard are endogenous parameters which, through physiological processes, exert an influence on the blood pressure, e.g., plasma volume, hematocrit, pulse, cardiac output per minute and electrolyte concentrations.

Further, it is possible to include measurement values which, during extracorporeal blood purification, via the transmembrane exchange will have an influence on the blood pressure, such as quantity and rate of the ultrafiltrate, composition and temperature of the dialysate, sodium balance and consumption of drugs.

Verbal information, e.g. subjective complaints of the patient, medical comments and additional instructions on therapy, are inputted as linguistic variables $L_1 \ldots, L_m$ into control device 10 via an input unit 14 preferably provided as a keyboard.

A measurement value processing unit 15 receives all input values $L_1 \ldots, L_m$ and $M_1 \ldots, M_n$ and from these derives further values $L_{11} \ldots, L_{mj}$ and $M_{11} \ldots, M_{n1}$, such as differences between measurement values, rates of changes, short- and long-term trends, which are essential for observing the course of the blood pressure and are used as input values for a semantic analyzer 16.

All values received and derived by the measurement value processing unit 15 are supplied to the semantic analyzer 16 which detects the significance of their contents for the different semantic domains. Semantic analyzer 16 forms the first hierarchical level of the control device. Since no precise (deterministic) medical knowledge exists on the semantic interdependencies between the input values and the semantic domains, a first fuzzy control unit 17 is used for semantic analysis.

FIG. 2a is a systematic diagram of the semantic domain "hypotension" processed in the first fuzzy control unit 17. This domain is divided into the subdomains "decrease of blood pressure" (BP decrease), "trend of hypotension" and "subjective complaints" and thus contains 64 ($4^3$) different conditions. Thus, the control base of the fuzzy control unit, developed in correspondence thereto, consists of a scale of conditions including 64 rules. To each condition, according to its significance for blood circulation, there is associated a drug dose $D^*_n$ determined by a corresponding rule and arranged in the form of a fuzzy set, as is evident in FIG. 4 by the example of two rules $D^*_n$ and $D^*_{n+1}$. The x-axis represents the whole range of doses, with the 64 rules being distributed along this axis corresponding to their dose.

Figure 2B:
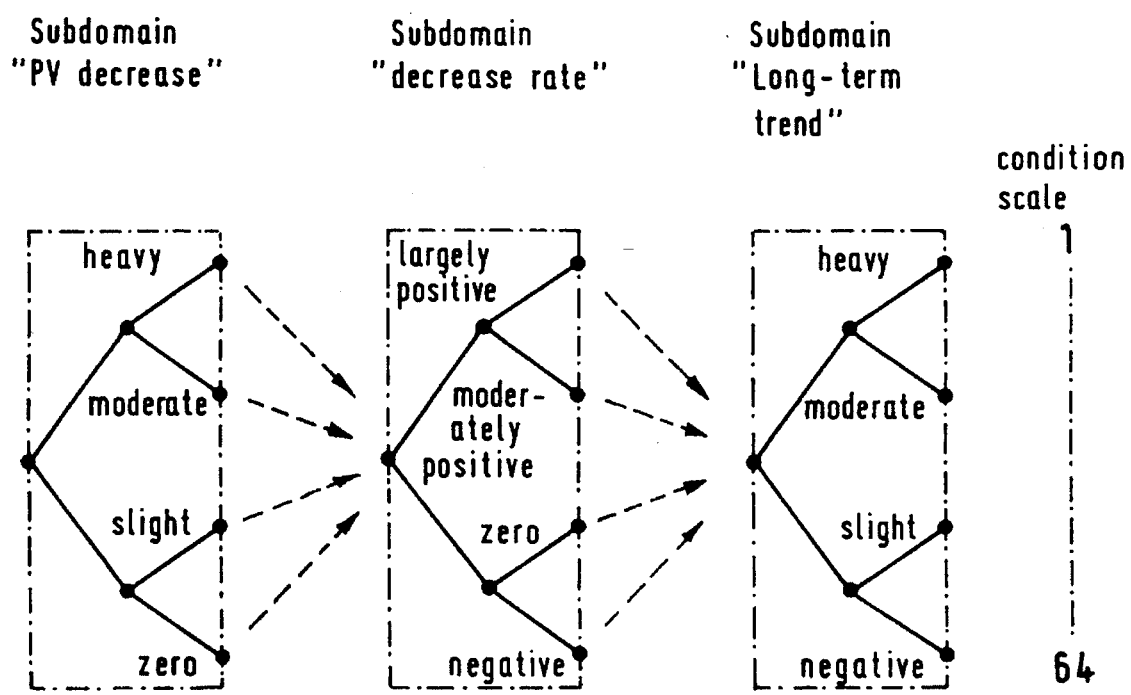
Figure 2C:
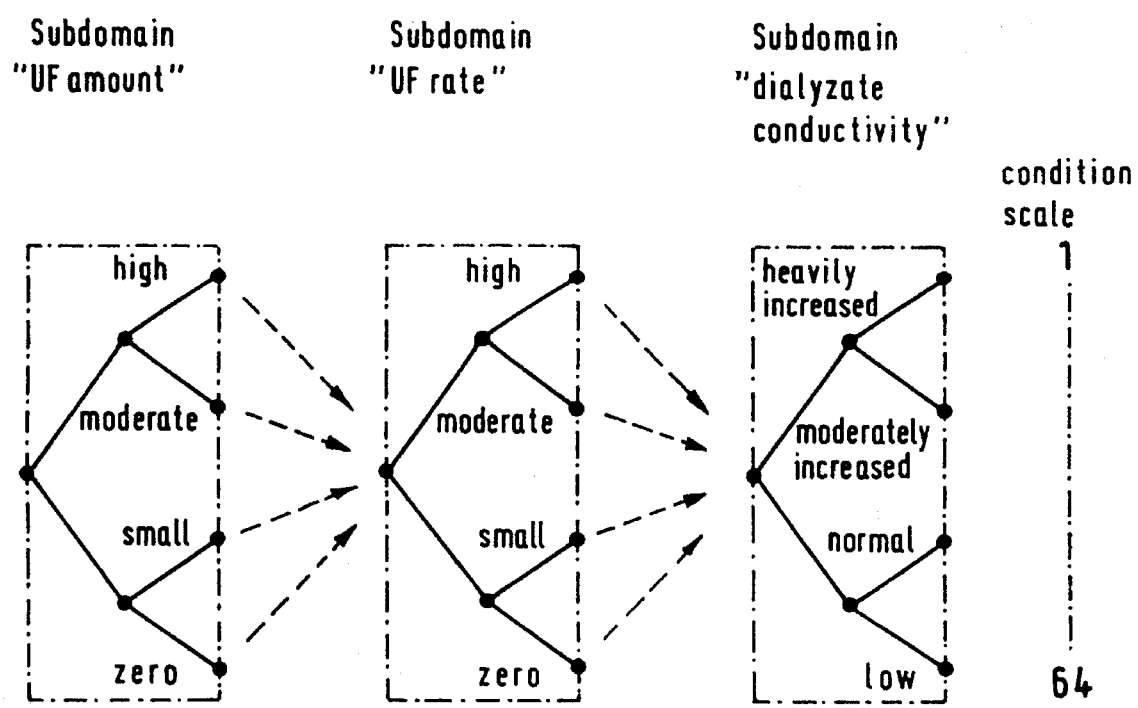

The large number of different components of influence relevant for blood pressure is exemplified by the semantic domains "plasma volume" in FIG. 2b and "ultrafiltration" in FIG. 2c. In these two domains, other than in FIG. 2a, the blood pressure itself is not used as a decision-making criterion.

In FIG. 3, an example is given of the membership functions of three different decision-making criteria to explain the manner in which the fuzzy sets for fuzzy knowledge are stored in the fuzzy control unit 17. FIG. 3a illustrates the membership functions 25 for the decision-making criterion "decrease of blood pressure" (BP decrease). The relative decrease of blood pressure $(P_0-P)/P_0$ is shown along the abscissa, $P_0$ being the predetermined desired blood pressure and P being the currently measured blood pressure. The grades-of-membership c are shown along the ordinate in a scale from "0" to "1". The decision-making criterion "decrease of blood pressure" has four linguistic variables associated thereto as symptom intervals in the form of fuzzy sets, i.e. the intervals "about zero", "small", "moderate" and "large". Each of these symptom intervals is of a trapezoidal shape. The trapezes can be symmetrical or asymmetrical, and they overlap each other.

For a specific current drop of blood pressure, indicated by A* in FIG. 3a, the grades-of-membership for the respective linguistic variables result from the points of intersection of the line A* with the membership functions.

FIG. 3b illustrates the membership functions 26 for the criterion "trend of hypotension". The four linguistic variables are "negative", "zero", "moderately positive" and "largely positive". Also in this case, fuzzification is performed by trapezoidal or triangular membership functions in a range of values 0 . . . 1. The current value is referred to as B*. In the illustrated example, the intersecting points of B* result in grades-of-membership >0 with the fuzzy sets "moderately positive" and "largely positive".

The third decision-making criterion "subjective complaints" according to FIG. 3c is provided to comprise statements on headaches, nausea and vomiting, which are inputted via keyboard 14 together with an assessment of the degree of their intensity. In the illustrated example, the current value C* for this decision-making criterion indicates identical grades-of-membership of 0.5 for the symptom intervals "small" and "moderate". The membership functions of FIG. 3c are designated by reference numeral 27.

In the semantic analyzer 16, the complex interaction between a plurality of influence values from different semantic domains is considered by a multi-stage inference process for semantic evaluation of the domains. For this purpose, in the first evaluation stage, the memberships to the individual symptom intervals for the 64 possible conditions—which memberships have been obtained according to FIG. 3—are aggregated to overriding memberships $c_{ges\ n}$ (n=1 . . . 64) by the fuzzy control unit 17 assisted by a quantity operator, e.g., a minimum operator. All conditions for which grades-of-membership >0 are obtained from the current facts A* as well as B* and C*, will be marked as activated conditions having an overriding membership >0.

On this basis, the first semantic evaluation value of the individual domains is detected by computing the center of gravity and the moment of the overriding memberships of all activated conditions of the domain. The moment of a semantic domain is the result of the position of the center of gravity of all overriding memberships of this domain.

Figure 4:
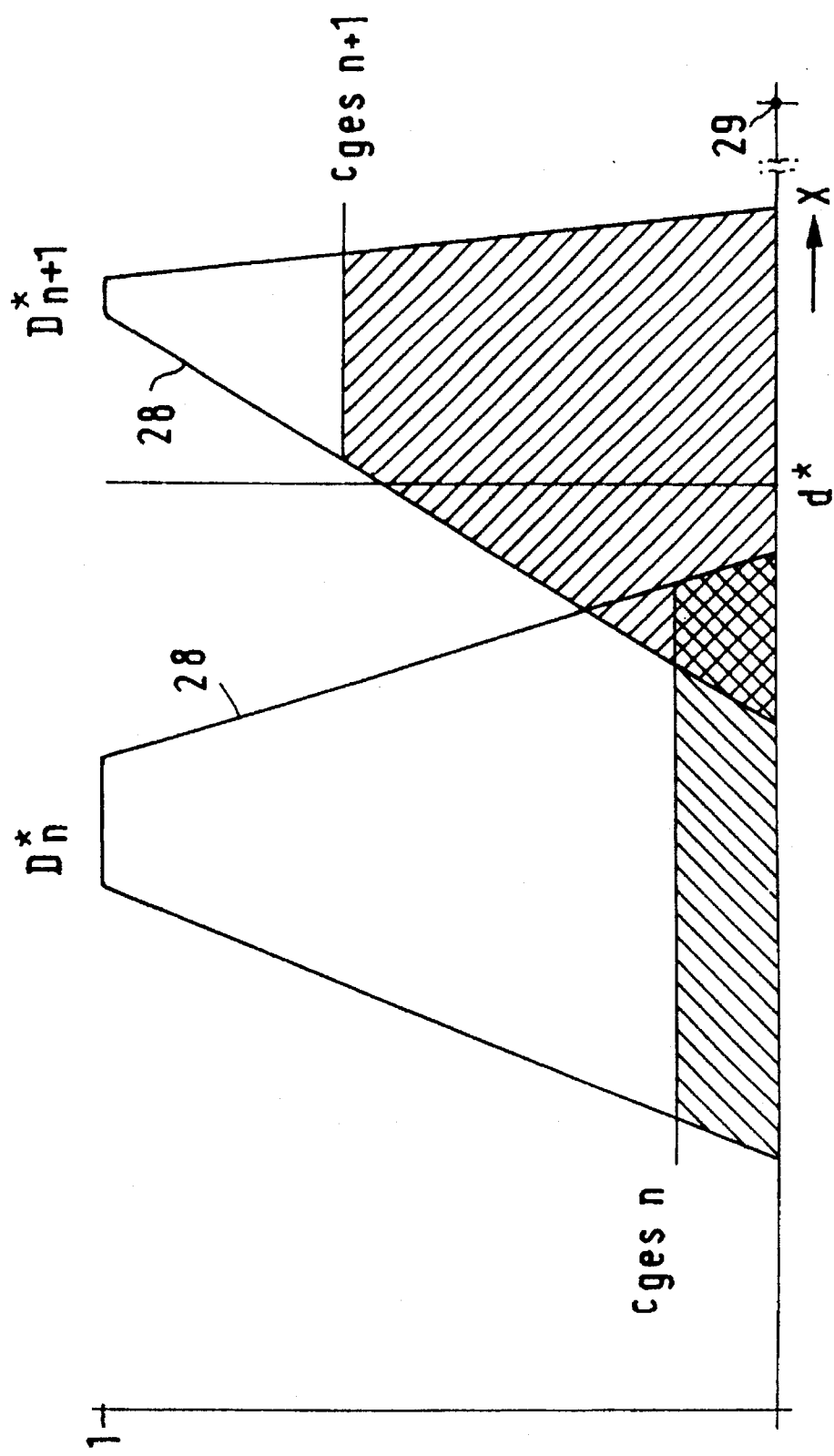
FIG. 4 illustrates the detection of the center of gravity and of the moment of the activated states.

FIG. 4 illustrates the computation of the center of gravity of a domain and the moment of this point, exemplified with reference to two activated conditions $D^*_n$ and $D^*_{n+1}$; in this example, n is a number from 1 to 64 on the condition scale and indicates the number of the condition in the respective domain. Each condition 28 is defined by a trapezoidal fuzzy set, with its position on the x-axis indicating its dosage range. The two surfaces marked by hatched lines correspond to the overriding memberships $C_{ges\ n}$ and $C_{ges\ n+1}$ which are obtained from the intersecting points of the current facts A*, B* and C* by the fuzzy sets of the respective domain. The center of gravity and the moment of both conditions are calculated from the size of the hatched surfaces and their position on the x-axis. d* is the abscissa value of the center of gravity of the two hatched surfaces, and the moment is the product of the distance of d* from the final value 29 of the condition scale and the surface area of the hatched surfaces.

Figure 5A:
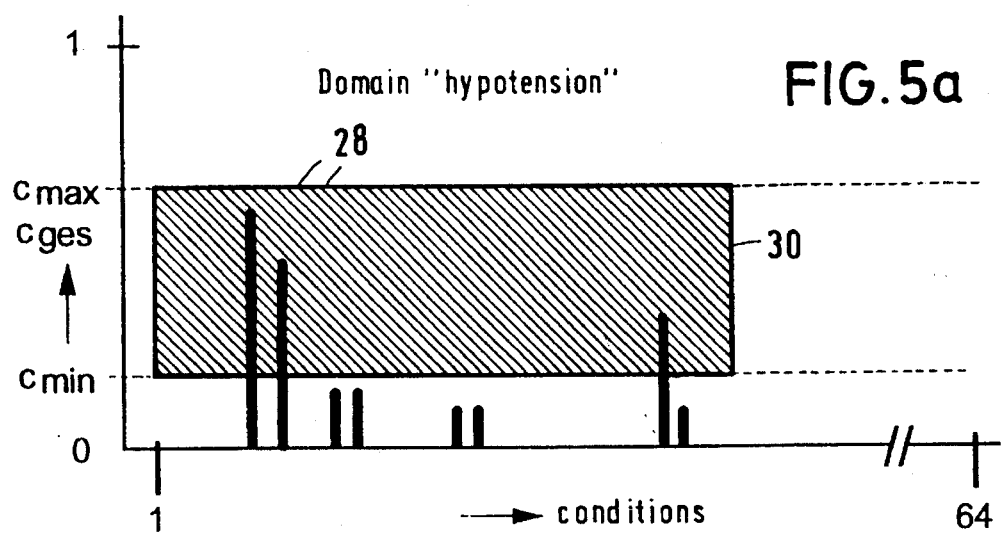
FIG. 5 illustrates the operation of the domain evaluating unit.
Figure 5B:
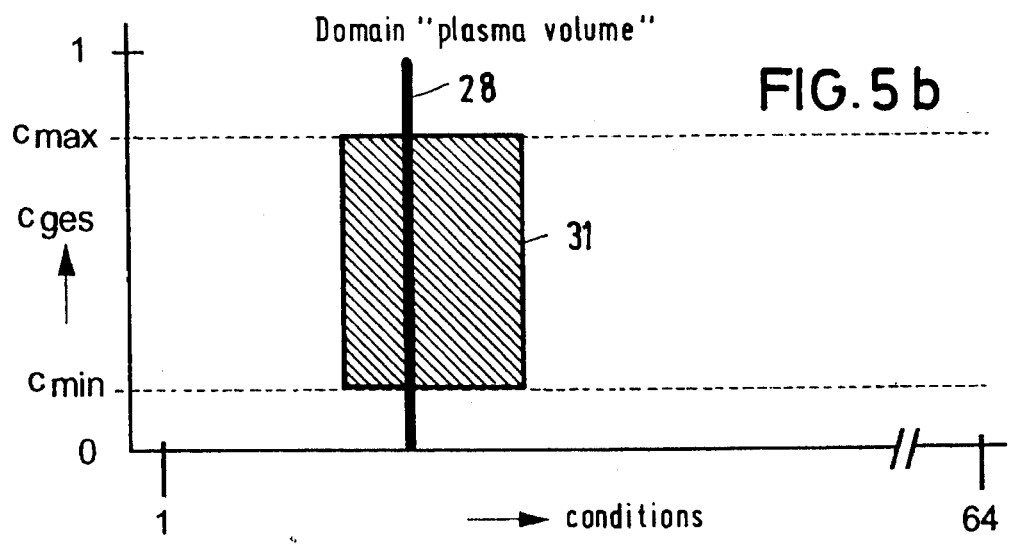
Figure 5C:
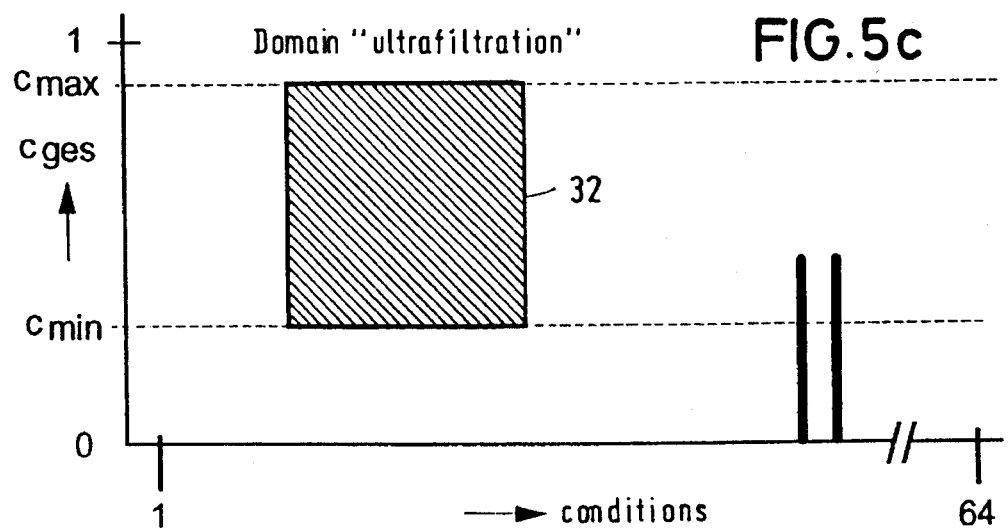

For further semantic evaluation, the semantic analyzer 16 is provided with a domain evaluation unit 18, operating in the manner illustrated in FIG. 5 with reference to the semantic domains "hypotension", "plasma volume" and "ultrafiltration" shown in FIGS. 2a–c. The domain evaluation unit 18 has stored therein the physician's knowledge on the medical ranking of the various conditions and the conclusions to be drawn therefrom in consideration of the computed moments of the individual domains. In the second semantic evaluation stage, each individual domain is weighted by a fixed factor. As a result of the second semantic evaluation stage, domain evaluation unit 18 determines to what extent the fuzzy control units of the second hierarchical level will participate in the computation of the quantities of the drugs or infusion rates to be administered by the connected infusion apparatus 21.

In the second semantic evaluation stage, after the fuzzy control unit 17 has computed the moments of all semantic domains in the first semantic evaluation stage, the overriding memberships $c_{ges\ n}$ of the activated conditions are analyzed according to FIG. 5 as to their localization relative to semantically determined fields 30,31,32 which are of eminent importance for medical decisions on dosage. The lines 28 in FIG. 5 are corresponding to the overriding memberships $c_{ges}$ as marked in FIG. 4 by the hatched surfaces of the conditions 28. As soon as at least one overriding membership touches such a field 30,31,32, the moment of the respective domain is given a weighting factor >1. The numerical values of these weighting factors can differ from each other according to their domains. For instance, if in FIG. 5 the moment of the domain "hypotension" is 0.8 and the predetermined weighting factor is 2, the obtained weighted moment will be 1.6. If, on the other hand, all activated conditions of a domain are situated outside the hatched field, as shown in the domain "ultrafiltration", the weighting factor is set to be 1, so that the moment and the weighted moment of this domain will be identical.

In the third semantic evaluation stage, the domain evaluation unit 18 analyzes whether there exist overriding memberships $c_{ges\ n}$ which exceed a predetermined maximum value $c_{max}$ and simultaneously intersect a hatched field, as illustrated in FIG. 5 in the domain "plasma volume". The third semantic evaluation stage allows weighting factors which are analogous to the second evaluation stage, as well as controversial weightings if a massively activated condition, as illustrated in the domain "plasma volume", from the medical viewpoint requires a largely or exclusively plasma-volume-controlled infusion. For instance, an exclusively plasma-volume-controlled infusion can be obtained in the third evaluation stage in that a weighting factor 1 is used for the domain "plasma volume" and the previous weightings for the domains "hypotension" and "ultrafiltration" are canceled by a weighting factor 0. The table below illustrates the above explained measures by simple numerical examples:

| Semantic domain | First evaluation stage Moment | Second evaluation stage | | Third evaluation stage | |
|---|---|---|---|---|---|
| | | Predetermined factor | Weighting moment | Additional factor | Semantic total valuation |
| Hypotension | 0.8 | 2.0 | 1.6 | 0 | 0 |
| Plasma volume | 0.6 | 4.0 | 2.4 | 1.0 | 2.4 |
| Ultrafiltration | 0.1 | 1.0 | 0.1 | 0 | 0 |

The above example relates to an extreme case. Normally, the values obtained in the semantic total evaluation will be >0 for all domains.

The fuzzy control units 2 thru u, designated by reference numeral 19, in the second hierarchical level automatically multiply their domain-specific inference results by the value for the overall semantic evaluation of their domain, indicated in the last (right) column of the table. A control value accumulator 20 combines the results of the individual domains to compute the total control value for the connected infusion apparatus 21. For this purpose, the sum of all semantic evaluation results is set to 100% and the inference results of the individual fuzzy control units 2 . . . u are multiplied by the corresponding percentage of their domain. This normalization to 100% safeguards that the predetermined maximum dose will never be exceeded even in case of high dose portions of the individual domains. The sum of the normalized percentages of all domains directly indicates the quantity of the drug or the infusion rate to be administered by the infusion apparatus 21.

We claim:

1. A control system for controlling an infusion apparatus, comprising:

a semantic analyzer, a measurement value processing unit for generating a plurality of input values for the semantic analyzer from at least one of a plurality of measurement values and a plurality of linguistic variables, the semantic analyzer comprising a first fuzzy control unit for combining the plurality of input values into semantic domains and for assigning each of the input values to a condition scale having a plurality of individual conditions, each of the domains being analyzed through stored fuzzy sets and the condition scale by detecting a membership grade for each of the individual conditions of the condition scale, an evaluation unit for weighting the membership grades according to their domain and for generating a semantic evaluation value for each domain, a second fuzzy control unit for each domain for generating a domain-specific control value based upon the membership grade of the respective domain and the semantic evaluation value, and a control value accumulator for combining the specific control values for a plurality of domains into a total control value for the infusion apparatus.

2. The system of claim 1, wherein a moment to be weighted for generating the semantic evaluation value is obtained from the membership grade of a domain by generating a center of gravity.

3. The system of claim 2, wherein the weighted moments of all domains form the semantic evaluation values.

4. The system of claim 3, wherein the evaluation of the membership grades is performed by factors having their amounts depending on whether or not membership grades are present in a semantically determined field of the membership diagram of the domain.

5. The system of claim 4, wherein a membership grade, when exceeding a predetermined limit value and being within the range of the semantically determined field, obtains an additionally increased factor.

* * * * *